US00PP08358P

United States Patent [19]

Bull

[11] Patent Number: Plant 8,358

[45] Date of Patent: Aug. 31, 1993

[54] IMPATIENS PLANT NAMED DOERTE

[76] Inventor: Norbert Bull, Gärtnersiedlung 2, 2351 Gönnebek, Fed. Rep. of Germany

[21] Appl. No.: 802,862

[22] Filed: Dec. 6, 1991

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

An Impatiens plant named Doerte characterized by its large, intense red-purple flowers, compact growth habit, solid green foliage, floriferous habit, and its suitability for pot plant, patio, bedding plant and hanging basket culture.

2 Drawing Sheets

The present invention relates to a new and distinctive cultivar of Impatiens plant, botanically known as Impatiens, and referred to be the cultivar name Doerte. The new cultivar was developed by me through controlled breeding by crossing seed or female parent identified as Seedling No. 8 with male or pollen parent identified as Seedling No. 14. Both parents are unreleased and propriety lines.

Asexual reproduction of the new cultivar by the inventor by terminal or stem cuttings taken at Gönnebek, Federal Republic of Germany has shown that the unique features of this new Impatiens are stabilized and are reproduced true to type in successive propagations.

The following characteristics distinguish the new Impatiens from both its parent varieties and other cultivated Impatiens of this type known and used in the floriculture industry:

1. Large flowers which are intense pink (red-purple) in color.
2. Compact growth habit.
3. Medium size, dark green foliage with no variegation.
4. Very floriferous habit.
5. Suitable for pot plant, patio, bedding plant and hanging basket culture.

Doerte has a flower color somewhat similar to but a more intense pink than the flower color of the cultivar Aglia. Doerte further differs from Aglia in its non-variegated green foliage, more compact growth habit, and its different flower shape.

The accompanying colored photographs illustrate the overall appearance of this cultivar, showing the colors as true as it is reasonably possible to obtain in a colored reproduction of this type. The photo at the top of sheet 1 comprises a top perspective view of a potted plant of Doerte. The bottom photo on sheet 1 shows a single flower (top side), and top and bottom views of a typical leaf. The photograph on sheet 2 shows the upper side and under side of typical flowers, a bud with attached spur, and the upper side and bottom side of typical leaves. Scales in centimeters are included to show the size of these parts.

The following is a detailed description of my new Impatiens cultivar based on plants produced under normal commercial practice at Gönnebek, Federal Republic of Germany.

Color references are made to The Royal Horticultural Society (R.H.S.) Colour Chart except where general terms of ordinary dictionary significance are used.

Parentage: Controlled cross between Bull Unnamed Seedling No. 8×Bull Unnamed Seedling No. 14.

Propagation:

*Type cutting.*—Stem 15–20 mm long will grow to 4–5 cm in 20 days.

*Time to initiate roots.*—8 days at 22° C. summer.

*Time to initiate roots.*—10 days at 20° C. winter.

*Rooting habit.*—Very good.

Plant Description:

*Form.*—Symmetrically mounded, self-branching.

*Habit of growth.*—Compact growth habit. Eight (8) weeks after sticking stem cuttings in 12 cm pots, plant is approximately 30 cm in diameter and 31 cm in height, measured from top of pot.

Foliage description:

(1) *Size.*—Medium length approximately 8–10 cm; width 3–4 cm at point of maximum width.

(2) *Shape.*—Generally ovate, with acute to acuminate tip and acute base; see photos.

(3) *Margin.*—Mildly serrated.

(4) *Color.*—(a) Young foliage upper surface: Dark green, approximately RHS 139A. (b) Under surface: Light green. (c) Mature foliage upper surface: Dark green, approximately RHS 139A. (d) Under surface: Light green (see photo).

(5) *Veination.*—Red veins on under side (see photo).

(6) *Variegation.*—None.

Flowering Description:

*Flowering habit.*—Flowers from leaf whorl in uniform manner.

*Natural flowering season.*—March until October.

*Flower buds.*—Typical; brown-red in color.

*Flowers borne.*—On pedicels red-purple in color.

*Quantity of flowers.*—Very floriferous (see photo). Flowers both mask the crown and occur above the leaf canopy.

*Spur.*—Downwardly curved from base of calyx, approximately 4–5 cm in length and red-purple in color.

*Longevity.*—Flowers are long lasting and non-fading.

Petals:

*Number of petals.*—Five (5).

*Shape.*—Generally heart-shaped (see photo).

*Color.*—Upper surface: Approximately 58B. It is noted that in the bottom photograph showing a single flower, the illustrated flower color is a deeper red-purple than the true color of 58B. Color very uniform. Under surface: Same as for top side, only slightly lighter.

*Size of flower.*—Large, approximately 6.5 cm in diameter.

Reproductive organs:

*Stamens.*—Five (5)

*Anthers.*—Hooded, color pink.

*Pollen color.*—White.

*Stigma.*—Five in number, pale yellow in color.

*Styles.*—Pale yellow in color.

*Ovary.*—5 in number, size 3–5 mm., green in color.

Disease Resistance: No disease problems noted to date.

I claim:

1. A new and distinct Impatiens plant named Doerte, as illustrated and described.

* * * * *

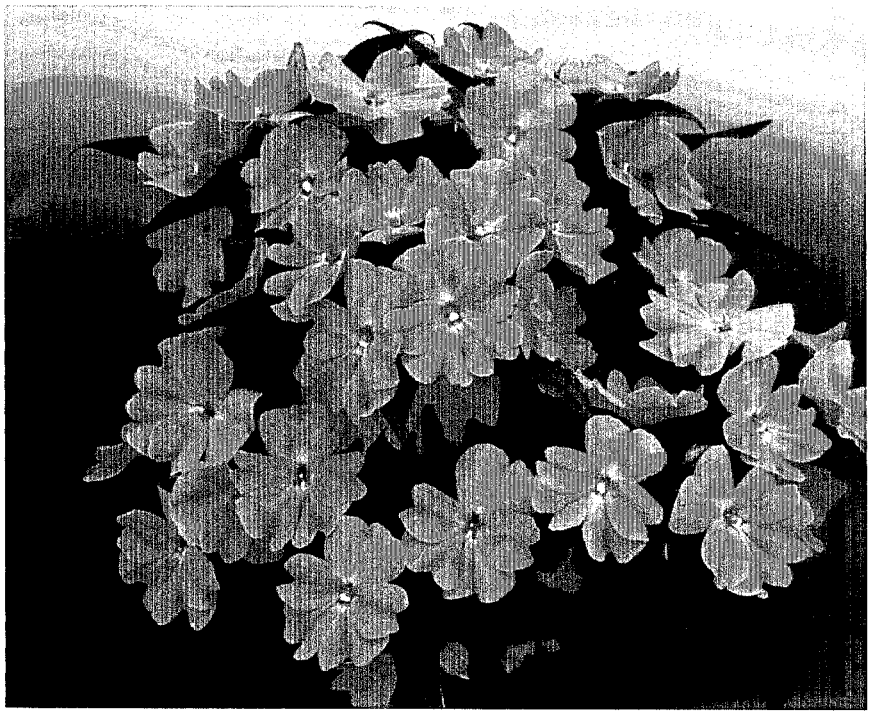
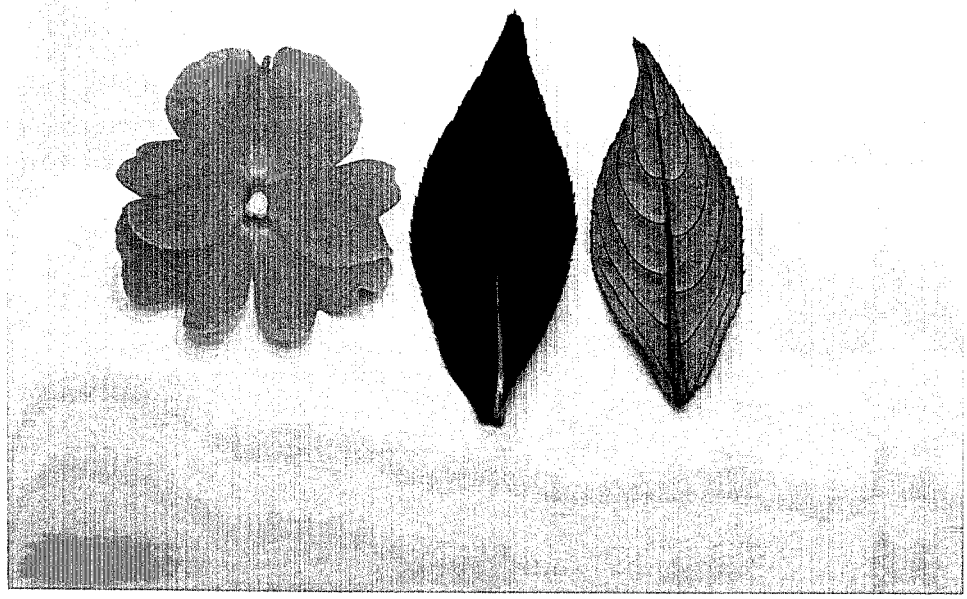

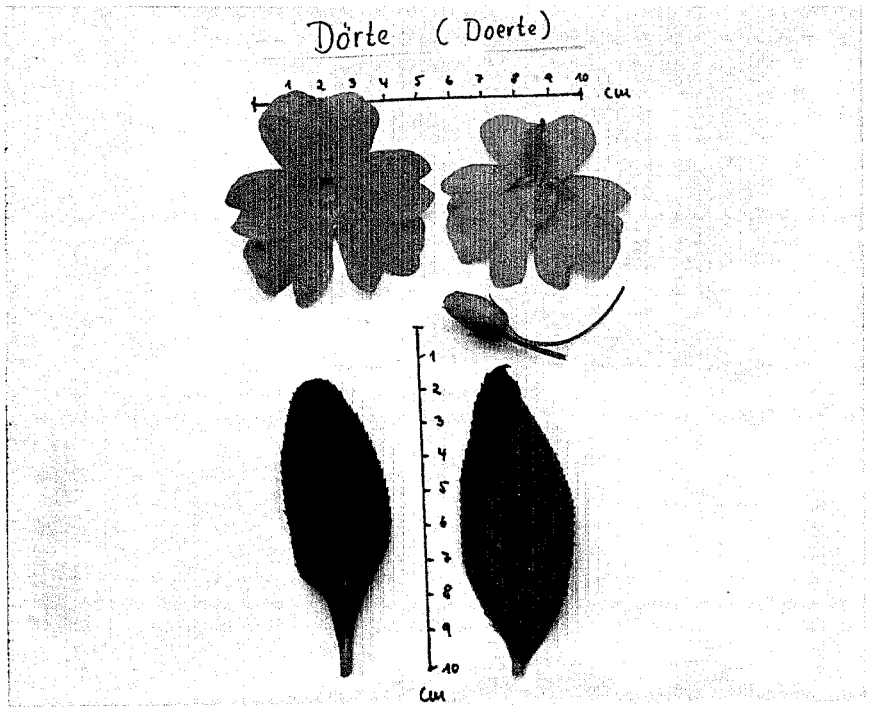
Dörte (Doerte)
1 2 3 4 5 6 7 8 9 10 cm
1 2 3 4 5 6 7 8 9 10
cm